(12) United States Patent
Mäyrä-Mäkinen et al.

(10) Patent No.: US 6,890,529 B1
(45) Date of Patent: May 10, 2005

(54) *LACTOBACILLUS HELVETICUS* PRODUCING ANTIHYPERTENSIVE DI- AND TRIPEPTIDES

(75) Inventors: Annika Mäyrä-Mäkinen, Helsinki (FI); Tarja Suomalainen, Helsinki (FI)

(73) Assignee: Valio LTD, Helsinki (FI)

(*) Notice: Subject to any disclaimer, the term of this patent is extended or adjusted under 35 U.S.C. 154(b) by 120 days.

(21) Appl. No.: 10/111,914

(22) PCT Filed: Oct. 30, 2000

(86) PCT No.: PCT/FI00/00941

§ 371 (c)(1),
(2), (4) Date: May 15, 2002

(87) PCT Pub. No.: WO01/32836

PCT Pub. Date: Oct. 30, 2000

(30) Foreign Application Priority Data

Nov. 1, 1999 (FI) ............................................. 19992360

(51) Int. Cl.[7] ........................... A01N 63/00; A23C 9/12; C12N 1/20
(52) U.S. Cl. ................... 424/93.45; 424/93.3; 424/93.4; 426/34; 426/42; 426/43; 426/61; 435/252.9
(58) Field of Search ........................ 424/93, 93.3, 93.4, 424/93.45; 426/34, 42, 43, 61; 435/252.9, 71.2; 514/18, 19; 530/800

(56) References Cited

U.S. PATENT DOCUMENTS

| 5,449,661 | A | | 9/1995 | Nakamura et al. |
| 5,541,111 | A | | 7/1996 | Yamamoto et al. |
| 5,695,796 | A | | 12/1997 | Yamamoto et al. |
| 5,766,940 | A | | 6/1998 | Yamamoto et al. |
| 5,854,029 | A | * | 12/1998 | Yamamoto ................. 435/71.2 |
| 6,399,140 | B1 | | 6/2002 | Allen et al. |
| 6,534,304 | B1 | | 3/2003 | Yamamoto et al. |

FOREIGN PATENT DOCUMENTS

| EP | 0 737 690 A2 | | 10/1996 | |
| EP | 0 821 968 A3 | | 7/1999 | |
| EP | 1016709 A1 | * | 7/2000 | ............ C12N/1/20 |
| GB | 2 294 191 A | | 4/1996 | |
| WO | 99/16862 | | 4/1999 | |
| WO | WO 9940798 A1 | * | 8/1999 | ............ A23C/21/00 |
| WO | WO 200132905 A1 | * | 5/2001 | ............ A23J/3/10 |

OTHER PUBLICATIONS

Catalog of Bacteria and Bacteriophages, 1989, American Type Cultur Collection, 17 th Edition, pp. 177, and 402.*
WPI, Derwent, accession No. 1994–268691, Calpis Shokuhin Kogyo KK: "Prepn. of peptide whichinhibits angiotensin conversion enzyme–by lactic acid bacterium culture of material with specified tri: peptide sequence"; & JP A 6197786, 19940719.
WPI, Derwent, accession No. 1986–110323, Calpis Shokuhin Kogyo KK: "Drug for prophylaxis of hypotension—contains high mol. substance obtd. by removing cell and casein from fermented milk", & JP 61053216, 19860317.
PAJ/JPO, "Peptide, Angiotensinase Inhibiting Composition and Their Production", Otsuka Shokuhin KK, &JP 9188694, 19970722.
Anne Pihlanto–Leppala et al; "Angiotensin I Converting Enzyme Inhibitory Peptides Derived from Bovine Milk Proteins", Int. Dairy Journal, vol 8, 1998, pp. 331.
Yamamoto Naoyuki et al; "Antihypertensive Effect of the Peptides From Casein by an Extracellular Proteinase from *Lactobacillus helveticus* CP790", J Dairy Sci., vol. 77, 1994, pp. 917–922.
Korhonen et al, Induction of Nitric Oxide Synthesis by Probiotic *Lactobacillus rhamnosus* GG in J774 Macrophages and Human T84 Intestinal Epithelial Cells, Inflammation, vol. 25, No. 4, Aug. 2001.

* cited by examiner

*Primary Examiner*—Christophet R. Tate
*Assistant Examiner*—Kailash C. Srivastava
(74) *Attorney, Agent, or Firm*—Nixon & Vanderhye

(57) ABSTRACT

The invention relates to a new strain, *Lactobacillus helveticus* LBK-16 H, DSM 13137, and a bacterial preparation containing the same. The new strain *Lactobacillus helveticus* LBK-16 H has proteolytic activity and is capable of promoting the production of nitric oxide, and thus it is useful both as a starter bacterium in dairy industry and as a therapeutic substance as such and in various health-promoting products and pharmaceuticals.

15 Claims, No Drawings

LACTOBACILLUS HELVETICUS PRODUCING ANTIHYPERTENSIVE DI- AND TRIPEPTIDES

This application is the US national phase of international application PCT/FI00/00941 filed 30 Oct. 2000, which designated the US.

FIELD OF THE INVENTION

The invention relates to a new microorganism and its use. More precisely, a new strain of *Lactobacillus helveticus*, its physiological characteristics, and its use e.g. in food industry and pharmaceutical industry are described.

BACKGROUND OF THE INVENTION

*Bergey's Manual of Systematic Bacteriology*, vol. 2, ed. by Sneath et al., Williams & Wilkins, Baltimore, London, Los Angeles, Sydney, 1984, Part 14, p. 1208 onwards, describes under title "Regular, Nonsporing Gram-Positive Rods" characteristics and classification of microorganisms belonging to the genus Lactobacillus as well as properties of the species *Lactobacillus helveticus*. Generally, *Lactobacillus helveticus* strains have been isolated from dairy products, such as fermented milk products and cheeses, and conventionally, they have been used as starter microbes in the manufacture of cheeses, particularly cheeses of Emmental and Gruyère type.

Biological effects of *Lactobacillus helveticus* strains have also been described in the prior art. For instance, international patent application WO99/16862, Yamamoto et al., describes the strain *Lactobacillus helveticus* CM4, FERM BP-6060 which is capable of producing a large amount of the tripeptide Val-Pro-Pro and/or Ile-Pro-Pro and which has high extracellular protease activity. The publication also describes fermented milk products containing the above-mentioned tripeptides and bacterium, and a method for the preparation thereof by fermenting products containing the tripeptide sequences with said bacterium.

U.S. Pat. No. 5,449,661, Nakamura et al., describes the preparation of a peptide containing the tripeptide sequence Val-Pro-Pro and its use for lowering hypertension. The peptide is prepared by fermenting fat-free milk with the strain *Lactobacillus helveticus* JCM 1004, whereafter the peptide is purified chromatographically and freeze-dried.

Yamamoto et al. have also described purification and characterization of a proteinase originating from the microorganism *Lactobacillus helveticus* CP790 (*J. Biochem*., 1993, 114:740). Moreover, Yamamoto et al. have also reported on a research in which $\alpha_{s1}$- and β-casein were hydrolysed with said proteinase and the obtained peptides were studied for their inhibitory effect on ACE (*J Dairy Sci*, 1994, 77:917). The studied peptides were 25 in total and their molecular sizes and effects differed greatly. The most efficient ones were three peptides obtained from β-casein and containing 8, 18 and 27 amino acids respectively. The study also compared ACE-activity of milk fermented with the strain *Lactobacillus helveticus* CP790 and its variant CP791 with defective proteinase activity, whereby the former was found effective in spontaneously hypertensive SHR rats but not in an ordinary rat strain, whereas the latter had no activity at all.

Even though lactic acid bacteria and also the species *Lactobacillus helveticus* have been widely studied and recommended for use both as a conventional starter and as a health-promoting substance, there is still a constant pursuit in the field of finding new, effective microbes which are useful both as starters and as probiotics in dairy and other food industries as well as natural products and also in pharmaceutical industry.

DESCRIPTION OF THE INVENTION

The object of the present invention is to provide a new strain of *Lactobacillus helveticus* having excellent proteolytic and physiological properties, and hence, being well suited for use both as a starter and as a health-promoting substance.

According to the present invention, the strain is provided for consumers to use as such or in the manufacture of edible foods, functional products or pharmaceuticals.

The present invention thus relates to *Lactobacillus helveticus* LBK-16 H, DSM 13137.

The present invention also relates to a bacterial preparation which contains the strain *Lactobacillus helveticus* LBK-16 H, DSM 13137.

The present invention further relates to the use of the strain *Lactobacillus helveticus* LBK-16 H, DSM 13137 in food industry or pharmaceutical industry.

The present invention still further relates to edible products, such as foodstuffs and pharmaceuticals, which contain or which have been prepared by using the above-described strain.

The invention also relates to the strain *Lactobacillus helveticus* LBK-16 H, DSM 13137 for use as a therapeutic substance.

The invention further relates to the strain *Lactobacillus helveticus* LBK-16 H, DSM 13137 for use in the treatment of hypertension.

The invention still further relates to the use of the strain *Lactobacillus helveticus* LBK-16 H, DSM 13137 for the preparation of antihypertensive products.

Furthermore, the present invention relates to a method of preparing an antihypertensive product, which method employs the strain *Lactobacillus helveticus* LBK-16 H, DSM 13137.

The invention is based on a new strain of *Lactobacillus helveticus*, LBK-16 H, which was deposited with the depository authority Deutsche Sammlung von Mikroorganismen Zellkulturen GmbH (DSMZ) at Mascheroder Weg 1b, D-38124 Braunschweig, Germany under accession number DSM 13137 on 3 Nov. 1999 and which has the following characteristics:

A *Lactobacillus helveticus* strain which is gram-positive and has rod-shaped, long cells. The growth temperature range is about 35 to 45° C., the optimum temperature being about 37 to 42° C.

*Lactobacillus helveticus* LBK-16 H grows well in milk at a temperature of 37 to 42° C. producing 2.5 to 2.9% of lactic acid (DL). The optimum pH for growth is about 4.5 to 7. In cultivation without pH adjustment, pH decreases in milk within the range of 3.3 to 3.6.

The strain also grows well in media commonly used for Lactobacilli and may also use citrate as a carbon source.

*Lactobacillus helveticus* LBK-16 H ferments carbohydrates as follows:

| Carbohydrate | L. helveticus LBK-16 H |
|---|---|
| Glycerol | − |
| Erythritol | − |
| D-arabinose | − |
| L-arabinose | − |
| Ribose | − |
| D-xylose | − |
| L-xylose | − |
| Adonitol | − |
| β-methylxyloside | − |
| Galactose | + |
| D-glucose | + |
| D-fructose | + |
| D-mannose | + |
| L-sorbose | − |
| Rhamnose | − |
| Dulcitol | − |
| Inositol | − |
| Mannitol | − |
| Sorbitol | − |
| α-methyl-D-mannoside | − |
| α-methyl-D-glucoside | − |
| N-acetyl-glucosamine | + |
| Esculin | − |
| Cellobiose | − |
| Maltose | − |
| Lactose | + |
| Saccharose | − |
| Trehalose | − |
| Inulin | − |
| Melezitose | − |
| D-raffinose | − |
| Glycogen | − |
| Xylitol | − |

*Lactobacillus helveticus* LBK-16 H is proteolytically active. Determined by the OPA method, described below in the examples and based on the proteolysis of o-phthaldialdehyde, the proteolytic activity of the strain is in the order of 0.3 to 0.6. Proteolytic activity can be utilized both for use as a starter are used and for the preparation of biologically active substances.

*Lactobacillus helveticus* LBK-16 H tolerates very well low pH values. This is an important property both from the viewpoint of preservability and physiological activity. As described in the examples, the strain tolerates very well a pH level of 4 and even 3 for four hours and its preservability especially in milk products is excellent, up to 4 hours in as low pH as pH 2. On the basis of the results, it can also be assumed that the strain survives the digestive tract past the stomach and remains viable in the colon.

*Lactobacillus helveticus* LBK-16 H also exhibits excellent tolerance to bile, it tolerates bile concentrations of up to 0.5%. This result also indicates that the strain survives the digestive tract through the stomach and the small intestine and remains viable in the colon.

*Lactobacillus helveticus* LBK-16 H has also been proved to have the ability to produce nitric oxide. The production of nitric oxide has been studied as the formation of nitric oxide provided by activation of nitric oxide synthetase. In the J774 macrophage cell line the strain produced 0.4 $\mu$M of NO, and in the T84 human enterocyte cell line about 2 to 6 $\mu$M of NO. This property is highly significant: activation of the NO production in an appropriate amount is advantageous, for instance in inflammation response and in blood pressure regulation.

*Lactobacillus helveticus* LBK-16 H has also been found to have the ability to produce bioactive peptides. It is described in the examples of Finnish patent application 992360 how a well preservable product containing antihypertensive peptides is prepared by a two-step method, in the first step of which the above-mentioned biologically active peptides are produced by fermenting e.g. various milk products with *Lactobacillus helveticus* LBK-16 H alone or with a combination of said strain and other lactic acid bacteria strains. According to the examples of the publication, *Lactobacillus helveticus* LBK-16 H produced the known antihypertensive tripeptides VPP (Val-Pro-Pro) and IPP (Ile-Pro-Pro) 13 to 15 mg/l and 6 to 8 mg/l, respectively. The publication states that a mixture of different peptides is formed in the fermentation reaction. When the duration of fermentation is sufficient, relatively small di- and tripeptides are obtained.

On the basis of the above-described characteristics, *Lactobacillus helveticus* LBK-16 H can be considered a probiotic organism.

*Lactobacillus helveticus* LBK-16 H is useful, for instance, as a conventional starter bacterium in dairy industry, for instance in the manufacture of fermented milk products and cheeses. Use in the manufacture of cheeses, particularly Emmental cheese, is regarded as a preferred embodiment.

*Lactobacillus helveticus* LBK-16 H can also be utilized very well in the manufacture of special products, such as fermented milk products, particularly sour milk and yogurt, containing bioactive peptides.

*Lactobacillus helveticus* LBK-16 H can further be used as a functional substance as such, in the manufacture of edible substances, or as an ingredient or additive in edible substances.

*Lactobacillus helveticus* LBK-16 H is produced by cultivating the bacterium, for instance, in MRS broth, in milk, such as raw milk, reconstituted milk powder milk or milk treated with ultrasound, or in a medium, such as Rogosa or MRS, commonly used for Lactobacilli, by using conventional procedures. Selection of suitable cultivation conditions and other parameters, such as temperature, pH and aeration, are obvious to the person skilled in the art. The temperature can be 30 to 45° C., for instance. Adjustment of pH may be needed.

*Lactobacillus helveticus* LBK-16 H can be cultivated alone to form a pure culture. The strain can also be cultivated as a mixed culture, for instance, together with other starter microbes known in the field. When desired, it is also possible to provide a mixed culture by cultivating microbes of different types separately and then combining the different microbes in desired proportions. The microbe combinations are appropriately selected such that the best possible properties are provided in the end product and the risk of contamination is eliminated.

After cultivation, the cell suspension is recovered and used as such or treated in the desired manner, for instance by concentrating, drying or lyophilizing.

Naturally, *Lactobacillus helveticus* LBK-16 H can also be used as a pure culture or mixed culture, separately or, for instance, with conventionally used and commercially available starters or probiotics.

In accordance with the invention, the bacterial preparation which is lyophilized and which contains the strain *Lactobacillus helveticus* LBK-16 H, DSM 13137, in an appropriate adjuvant, is regarded as a preferred preparation.

The bacterial preparation of the invention may contain the above bacterium as such or combined with other constituent components, such as other microorganisms.

In accordance with the present invention, the strain can also be used in the manufacture of edible products, particularly (functional) foods, natural products or pharmaceuticals.

The edible products of the invention are prepared by using *Lactobacillus helveticus* LBK-16 H, DSM 13137, or a bacterial product containing the same, and conventional ingredients of (end) products. The bacterium can be added to a food or other product during the manufacturing process thereof, or to a finished product. It is also possible to use the bacterium in connection with the manufacture of the product such that no bacterial cells but only products produced during the bacterial growth, such as flavoring and aromatic substances or substances having biological activity, remain in the end product.

In the present document, the term food is used in a broad sense covering all edible products which can be in solid, gelled or liquid form, and covering both ready-to-eat products and products to which the product of the invention is added in connection with consumption, as a supplement or to be a constituent component of the product. For instance, the foods can be products of dairy industry, meat processing industry, food processing industry, beverage industry, baking industry and confectionery industry. Typical products include milk products, such as fat-free milk, milk with various fat contents as such or in the form of corresponding milk powder, and fermented milk products, such, as sour milk, buttermilk, curd cheese, yogurt, curdled milk, unripened cheeses and ripened cheeses, snack fillings, etc. Beverages, such as whey beverages, fruit beverages and beers, constitute another important group.

In connection with the present invention, products of pharmaceutical industry include, apart from various pharmaceutical preparations, also health-promoting natural products and the like. Typical forms of preparations are capsules, pills and solutions, for instance.

In accordance with the invention, *Lactobacillus helveticus* LBK-16 H, DSM 13137, is used in a sufficient amount to provide the desired effect. The amount to be used may thus vary within a wide range, depending on the application and the effect.

In the following, the invention will be described in greater detail by means of examples. These examples are only intended to illustrate the invention, not to restrict its scope in any way.

EXAMPLE 1

Cultivation of the Strain *Lactobacillus helveticus* LBK-16 H

The strain *Lactobacillus helveticus* LBK-16 H was cultivated by inoculating a stock strain twice in MRS or milk broth with 1% inoculum at a temperature of 37° C. for 20 to 24 hours. The actual (productional) cultivation was also carried out in MRS-based or milk-based broth at a cultivation temperature of 35° C. to 42° C. by growing the strain for 20 to 48 hours (with or without pH adjustment).

The cells can be recovered from the cultivation as such or the cells can be concentrated by utilizing known techniques and used as a cell concentrate, or after the concentration they can also be freeze-dried to a powder-like product.

EXAMPLE 2

Proteolytic Activity of the Strain *Lactobacillus helveticus* LBK-16 H

The proteolytic activity of *Lactobacillus helveticus* LBK-16 H was determined from milk by means of the OPA method (Church, F. C., Swaisgood, H. E., Porter, D. H., Catigna, G. L., 1983, Spectrophotometric assay using o-Phthaldialdehyde for determination of proteolysis in milk and isolated milk proteins, *J Daily Sci* 66:1219–1227).

For carrying out the method, the bacterial cells were cultivated in MRS broth in a tube of 10 ml, whereafter the suspension was washed with 0.9% NaCl and suspended to 10 ml. The bacterial cells were inoculated as 1% inoculum to 10 ml of 22-degree milk. A corresponding milk sample without a bacterial inoculum was used as a control.

2.5 ml of the sample, 0.5 ml of water and 0.5 ml of 0.75 N trichloro acetic acid (TCA) were mixed well in a Vortex device, allowed to rest for 10 minutes and filtered through the Whatman #2 filter paper. A 150 μl sample was taken from the TCA filtrate and mixed with 3 ml of OPA reagent in a disposable cuvette. The mixture was incubated for 2 minutes at room temperature, whereafter it was measured with a spectrophotometer at a wavelength of 340 nm. The control value was subtracted from the reading, whereby the proteolytic activity of *Lactobacillus helveticus* LBK-16 H became 0.3 to 0.6.

OPA reagent:

25 ml of 100 mmol sodium metaborate 2.5 ml of 20% (w/w) SDS 40 mg of OPA (o-phthaldialdehyde) dissolved in 1 ml of methanol 100 μl of β-mercaptoethanol The substances are combined and dissolved in water so that the final volume is 50 ml. The reagent preserves one day stored in the dark.

EXAMPLE 3

The pH Tolerance of *Lactobacillus helveticus* LBK-16 H

LBK-16 H was cultivated for 17 to 18 hours in MRS broth twice before the test. Thereafter, the strain was cultivated for the test either in MRS broth or milk broth. In pH testing, the pH of the test broth (MRS) was adjusted to pH 6.5, pH 4 and pH 2 (with lactic acid). These broths were inoculated with MRS or milk broth cultivations such that the initial concentration was $10^7$ cfu/ml, and cultivated for 3 and 4 hours at 37° C., whereafter the concentration of the strain LBK-16 H was determined from the cultivations (by the determination method of Lactobacilli on MRS agar). The results are presented in Table 1.

TABLE 1

The pH tolerance of the strain LBK-16 H

| | initial concentration | 3 hours | | | 4 hours | | | |
|---|---|---|---|---|---|---|---|---|
| | | pH 6.5 | pH 4 | pH 3 | pH 6.5 | pH 4 | pH 3 | pH 2 |
| MRS | $4 \times 10^7$ | $6 \times 10^7$ | $3 \times 10^7$ | $5 \times 10^7$ | $6 \times 10^7$ | $3 \times 10^7$ | $3 \times 10^7$ | <100 |
| Milk | $5 \times 10^7$ | $5 \times 10^7$ | $3 \times 10^7$ | $6 \times 10^7$ | $5 \times 10^7$ | $4 \times 10^7$ | $7 \times 10^7$ | $1 \times 10^4$ |

The strain thus tolerates very well the pH level of 4 and even 3 for four hours. The preservability of the strain at a level as low as pH 2/4 hours when ingested in a milk product is better than in an aqueous product.

EXAMPLE 4

Bile Tolerance of the Strain *Lactobacillus helveticus* LBK-16 H

LBK-16 H was cultivated as in Example 3. The testing was carried out in MRS broths, to which bile acid, Bile Bovine; Sigma B-3883, was added in the amount of 0.3% and 0.5%. 1% of fresh culture from the MRS- or milk-based cultivations was added to the bile-containing broths, the initial concentration being 2–5×10$^6$ cfu/ml. The strain was cultivated in the broth for 3 hours, whereafter the cell concentration on MRS agar was determined. The results are presented in Table 2.

TABLE 2

| | Bile tolerance of LBK-16 H | | |
|---|---|---|---|
| | | Bile concentration | |
| growth medium | 0 | 0.3% | 0.5% |
| MRS | 2 × 10$^6$ | 2 × 10$^6$ | 4 × 10$^5$ |
| Milk | 5 × 10$^6$ | 6 × 10$^6$ | 5 × 10$^6$ |

As appears from the table, LBK-16 H tolerates bile concentrations of up to 0.5%.

EXAMPLE 5

Production of Nitric Oxide by *Lactobacillus helveticus* LBK-16 H

The production of nitric acid by *Lactobacillus helveticus* LBK-16 H was studied using the method described by Korhonen et al. (Induction of nitric oxide synthesis by probiotic Lactobacillus GG in J774 macrophages and T84 colon epitheal cells, Korhonen, R., Korpela, R., Saxelin, M., Mäki, M., Kankaanranta, H. and Moilanen, E., Submitted). The method is based on induction of an inducible nitric oxide synthetase (iNOS) and the resulting production of nitric oxide (NO). Two different cell lines were used in the test: J774 murine macrophage cell line and T84 human enterocyte cell line. The induction was carried out in the J774 cell line with *Lactobacillus helveticus* LBK-16 H cells in the presence of γ-interferon, because the bacterial cells alone did not produce NO. The proportion of the cells of the cell line and the bacterial strain was 1:10.

Expression of the enzyme iNOS was determined by the Western blot technique using lipopolysaccharide (LPS) and lipoteicoic acid (LA) as references.

The production of nitric oxide (NO) was determined in the amount of the nitric oxide metabolite nitrite in the growth medium after 24 hour incubation. The nitrite amount was measured by Griess reaction (Green et al., 1988, *Analytical Biochemistry*, vol. 126, pp. 131 to 138).

*Lactobacillus helveticus* LBK-16 H was capable of producing 0.4 μM of nitric oxide in the murine macrophage cell line and 5 to 6 μM of nitric oxide in the human epitheal cell line. For the sake of comparison, it can be mentioned that *Lactobacillus rhamnosus* LC 705, DSM 7061, produced only 0.7 μM of nitric oxide in T84 cells.

EXAMPLE 6

Production of Bioactive Peptides by *Lactobacillus helveticus* LBK-16 H

The strain *Lactobacillus helveticus* LBK-16 H was cultivated in MRS broth at 37° C. for 24 hours and was inoculated to reconstituted milk (10%) in order to form an inoculum. After two cultivation rounds the inoculum (15%) was inoculated to a fermentor medium, which consisted of 9 to 10% fat-free milk powder milk and which was sterilized at 110° C. for 10 min. Fermentation was carried out at 37° C. for 22 to 24 hours, vigorously mixing all the time.

To perform a comparative test, the fermentation was repeated by using (a) a mixture of several strains, i.e. *L. helveticus* LB161, *L. helveticus* LBK-16 H and *L. helveticus* LB230, (b) a mixture of the strains *L. helveticus* LBK-16 H and *L. rhamnosus* LC705, DSM 7061, and (c) a mixture of the strains *L. helveticus* LBK-16 H and *Streptococcus thermophilus* T101, DSM 4022.

The growth medium employed was 9% milk which was sterilized at 100° C. for 15 min. To form inocula, the strains *L. helveticus* and *L. rhamnosus* LC705 were cultivated for 24 hours at 37° C. in MRS broth, wherefrom a 1% inoculum was then transferred to milk. *Str. thermophilus* T101 was cultivated for 18 hours at 37° C. in LM17 broth, wherefrom an inoculum was transferred to milk.

The first cultivation was carried out by cultivating all strains separately in milk, incubation at 37° C. for 24 hours. For the second cultivation, 1% of the strain of each mixture was pipetted into milk, whereafter co-cultivation was continued for 24 hours at 37° C. For the third cultivation, 5 to 10% of the above obtained co-cultivation was pipetted into milk and incubated at 37° C. for 24 hours.

The VPP and IPP amounts produced by the strain *L. helveticus* LBK-16 H and the different microbial mixtures are shown in Table 3. *Lactobacillus helveticus* LBK-16 H of the invention is capable of producing large amounts of bioactive peptides. The other microbes of the different mixtures did not produce bioactive peptides, but they did not interfere with the activity of LBK-16 H, either. No difference was observed between the mixtures or with respect to the strain LBK-16 H solely.

TABLE 3

| IPP and VPP amounts produced by strain LBK-16 H and different microbial mixtures | | |
|---|---|---|
| Microbe (mixture) | VPP, mg/l | IPP, mg/l |
| L161 + LBK-16H + LB230, 5% | 13–14 | 6–7 |
| L161 + LBK-16H + LB230, 10% | 13–14 | 6–7 |
| LBK16H + LC705, 5% | 13–14 | 6–7 |
| LBK16H + LC705, 10% | 13–14 | 6–7 |
| LBK16H + Str.T101 10% | 13–15 | 6–8 |
| LBK16H (solely) | 13–15 | 6–8 |

What is claimed is:

1. A biologically pure culture of *Lactobacillus helveticus* LBK-16H, DSM 13137.

2. A bacterial preparation comprising a biologically pure culture of *Lactobacillus helveticus* LBK-16H, DSM 13137.

3. A bacterial preparation as claimed in claim 2, further comprised of other microorganisms.

4. A bacterial preparation as claimed in claim 2, wherein the preparation is in the form of lyophilized powder or a capsule.

5. A method of manufacturing an edible or natural product comprising cultivating the biologically pure culture of *Lactobacillus helveticus* LBK-16H, DSM 13137 according to claim 1.

6. A method of manufacturing an edible or natural product as claimed in claim 5, wherein the product is selected from the group consisting of a milk product and a beverage.

7. An edible product comprising the pure culture according to claim 1, or the bacterial preparation according to claim 2.

8. An edible product as claimed in claim 7, wherein the edible product is a milk product.

9. An edible product as claimed in claim 7, wherein the edible product is a beverage.

10. A method of promoting health comprising administering to a subject in need thereof an effective amount of a biologically pure culture of *Lactobacillus helveticus* LBK-16H, DSM 13137 as an edible product or a pharmaceutical.

11. A method of promoting health as claimed in claim 10, wherein the subject has hypertension.

12. An antihypertensive product comprising a biologically pure culture of *Lactobacillus helveticus* LBK-16H, DSM 13137.

13. An antihypertensive product as claimed in claim 12, wherein the antihypertensive product further comprises antihypertensive di- and tri-peptides.

14. An antihypertensive product as claimed in claim 12, wherein the antihypertensive product further comprises at least one tripeptide selected from the group consisting of Ile-Pro-Pro and Val-Pro-Pro.

15. An edible product as claimed in claim 9, wherein the beverage is selected from the group consisting of whey beverage, fruit beverage and beer.

* * * * *